United States Patent [19]

Lyon et al.

[11] 4,231,376
[45] Nov. 4, 1980

[54] PRESSURE SENSOR

[75] Inventors: Warren C. Lyon, Baltimore; William H. Hayes, Jr., Woodbine, both of Md.

[73] Assignee: Hittman Corporation, Columbia, Md.

[21] Appl. No.: 931,526

[22] Filed: Aug. 7, 1978

Related U.S. Application Data

[63] Continuation of Ser. No. 698,895, Jun. 23, 1976, abandoned, which is a continuation of Ser. No. 488,988, Jul. 16, 1974, Pat. No. 4,027,661.

[51] Int. Cl.$^2$ ............................................. A61B 5/00
[52] U.S. Cl. ...................................... 128/748; 73/729; 128/659
[58] Field of Search ........... 128/748, 659, 673, 350 R, 128/350 V; 250/336 R; 73/729, 706

[56] References Cited

U.S. PATENT DOCUMENTS

| Re. 26,335 | 1/1968 | Chope | 73/398 |
|---|---|---|---|
| 3,034,356 | 5/1962 | Bieganski et al. | 128/2.05 E |
| 3,187,181 | 6/1965 | Keller | 250/360 |
| 3,503,402 | 3/1970 | Schulte | 128/350 |
| 3,625,199 | 12/1971 | Summers | 128/2.05 E |
| 3,686,958 | 8/1972 | Porter et al. | 73/406 |
| 3,757,770 | 9/1973 | Brayshaw et al. | 128/2 R |
| 3,789,667 | 2/1974 | Porter et al. | 73/406 |
| 3,834,239 | 6/1974 | King | 73/729 X |

OTHER PUBLICATIONS

Bustard, T. S. et al., *IEEE Trans. on Nucl. Science*, vol. 21, No. 1, Feb., 1974, pp. 697-701.
Lyon, W. C., *Hittman Associates Contract Report* #AT(-11-1)-3206, Jun., 1972.

*Primary Examiner*—Kyle L. Howell
*Attorney, Agent, or Firm*—Fleit & Jacobson

[57] ABSTRACT

A pressure sensor apparatus primarily for sensing pressure in a body cavity such as the cranium, bladder or vena cava of an animal or human comprising a housing having a bellows defining a chamber within the housing. Means is provided for communicating pressure from the body cavity to the chamber. A radioactive material is housed in the housing and at least partially surrounded by radiation shielding. The radiation shielding shields the radioactive material as a function of the pressure sensed by the flexible member and the radioactivity is sensed by a radiation detector.

8 Claims, 3 Drawing Figures

PRESSURE SENSOR

This is a continuation of Ser. No. 698,895, filed June 23, 1976, now abandoned, which is a continuation of Ser. No. 488,988, filed July 16, 1974, now U.S. Pat. No. 4,027,661.

CROSS-REFERENCE TO RELATED APPLICATION

This application is related to commonly assigned application Ser. No. 478,763, filed June 12, 1974, for PRESSURE SENSOR APPARATUS, by Thomas S. Bustard et al, now abandoned.

BACKGROUND OF THE INVENTION

The need for a non-invasive technique for measuring the pressure in body cavities of animals or humans is recognized as highly desirable for continuous or intermittent monitoring of body conditions. Such cavities as the cranium, vena cava, bladder, and others provide valuable and sometimes critical information for maintaining the well being or survival of an animal or human. For example, it is known that intracranial pressure provides a valuable indication of well being for a variety of clinical conditions.

A long-term, non-invasive monitor of intracranial pressure is particularly desirable for the congenital hydrocephalic. This condition is one in which the normal production of cerebralspinal fluid is not balanced by reabsorption of the fluid. The retained fluid increases the intracranial pressure and causes head swelling which is a characteristic of hydrocephalus. The increase in intracranial pressure can eventually lead to disability or death.

The normal treatment for hydrocephalus comprises surgically implanting a fluid shunt to transfer cerebrospinal fluid from the intracranial cavity to other parts of the body such as the peritoneal cavity or the jugular vein. The surgically implanted shunt is basically a drainage tube which contains a check valve and requires a modest pressure differential for the cerebrospinal fluid to flow. These shunts often become partially or even fully blocked and intracranial pressure starts to rise resulting in intracranial hypertension.

The symptoms characteristic of a blocked shunt are also characteristic of various other maladies. Early symptoms of a clogged shunt are nausea, headache, and dizziness, any of which can result from many other causes other than intracranial hypertension. In young children especially a physician cannot easily determine shunt blockage without performing a surgical procedure. The presence of an indwelling pressure sensor would permit the physician to directly monitor the intracranial pressure and remove a substantial amount of the risk from his diagnosis.

An additional problem associated with a blocked vent is the rate at which the pressure can rise. Drastic increases can occur within less than an hour. Since a high pressure that is maintained for a period of time will cause irreversible brain damage, it is imperative that pressure increases be discovered in the shortest possible time. Full utilization of a pressure sensor requires a simplified determination of the pressure so that even a parent can perform the determination.

Against this background, there is a recognized and long felt need for a device which overcomes the aforementioned disadvantages and provides a sensor having a self-contained, long-term energy source with compensation for ambient pressure variations and low sensitivity to temperature changes.

The pressure sensor of the pressure invention is designed to eliminate many of the previously mentioned problems. Once the pressure sensor is installed by a competent surgeon, the pressure can be read non-invasively by a physician with a minimal amount of special equipment. If an attending physician is not readily available, equipment can be installed in the child's home and the parents instructed in its use.

SUMMARY OF THE INVENTION

The pressure sensor of the present invention is fully implantable and contains a radioactive material so that the pressure can be readout non-invasively. In its preferred form, the sensor system comprises a housing having a chamber defined therein by a resilient bellows. Non-radioactive fluid is contained in the chamber and is in communication with a flexible member placed in the body cavity and exposed to the pressure to be sensed. The housing is located external to the cavity being sensed and preferably situated just under the skin. The housing contains a radioactive material at least partially surrounded by radioactive shielding. Either the radioactive material or the radioactive shielding is connected to the bellows. The pressure acting upon the flexible member causes the bellows to expand and contract. The movement of the bellows causes the radioactive shielding to shield the radioactive material as a function of the pressure sensed. The radioactivity is sensed from outside the skin by a conventional nuclear counter or crystal detector instrument.

The application of the present invention to hydrocephalus greatly facilitates treatment of the defect. The pressure sensor of the present invention when used as an intracranial pressure sensor device has a long life, is fully implantable and does not require any energy source other than the radioactive material contained in the device. Two of the major advantages of the present invention are the elimination of implanted energy sources, such as batteries, to operate the device, and the elimination of leads or other penetrations through the skin to provide power or transmit a signal. With a long-lived radioisotope such as promethium 145, the inventive pressure sensing device can be fully implanted and left in place for the life of the patient. Furthermore, the invention contemplates a design and a selection of materials that will assure a negligible radiation dosage to the patient. Although in this application, the invention is primarily intended for a long-term implantation in hydrocephalic children, one may easily appreciate its value in short-term monitoring of head trauma patients.

The inventive pressure monitoring system can be fully implanted with no tubing or wires penetrating the skin, functions accurately to within several millimeters of water pressure and is unaffected by variations in ambient pressure. Also, it is generally insensitive to ambient temperature. Furthermore, the materials used to construct the devices according to the present invention are biologically inert and do not pose any health hazard to the animal or human subject or make the subject more susceptible to mechanical trauma. The sensor unit is of relatively small size and so does not produce unsightly bulging when implanted subdermally.

Other features and advantages of the invention will be apparent from the following description of the preferred embodiments of the invention as shown in the accompanying drawings.

DESCRIPTION OF THE PREFERRED EMBODIMENTS

Figure 1:
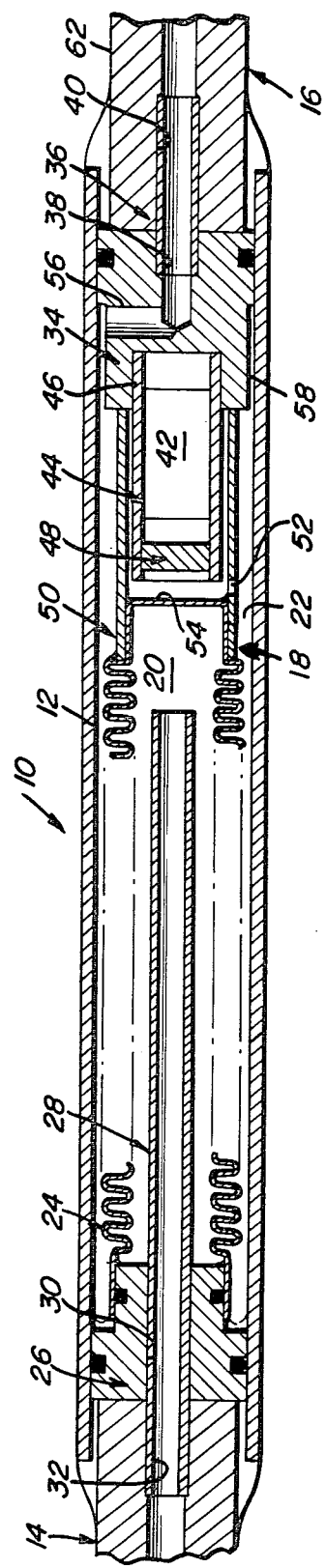
FIG. 1 is a vertical, cross-sectional view of one embodiment of the pressure sensor apparatus of the present invention.

Pressure sensor 10 broadly comprises housing 12 and flexible containers or tambours 14 and 16. Housing 12 defines an interior opening 18 which is divided into two chambers 20 and 22, respectively, by bellows 24. Chambers 20 and 22 act as reservoirs for non-radioactive fluid.

Bellows support 26 is mounted in the end of housing 12 and closes chamber 20. Chamber 20 is fluidly connected to tambour 14 by means of bellows tube 28 which fits into port 30 of bellows support 26 and opening 32 in the end of tambour 14. Chamber 22 is closed by radioactive material tube support 34 which is mounted in the other end of housing 12 from bellows support 26. Chamber 22 is fluidly connected to tambour 16 by means of connection tube 36 which fits into port 38 in radioactive material tube support 34 and into opening 40 in the end of tambour 16.

The radioactive material 42 is housed in source tube 44 which is mounted in opening 46 in radioactive material tube support 34. The open end of source tube 44 is closed by shield plug 48. Surrounding source tube 44 is shield tube 50 which is connected to bellows 24. Opening 52 in shield tube 50 places the face 54 of bellows 24 in communication with tambour 16 though port 56 in the body of radioactive material tube support 34 and annular opening 58 formed between housing 12 and radioactive material tube support 34.

Figure 2:
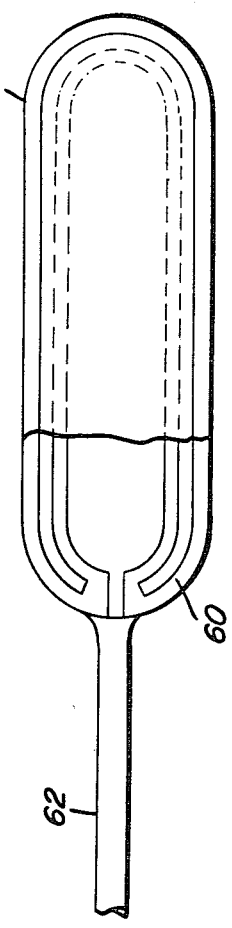
FIG. 2 is a plan view, partly in section, of one of the flexible tambours a portion of which is shown in FIG. 1.

Tambour 16 is filled with a non-radioactive fluid and is placed in the body cavity such as the cranium, bladder, on vena cava of an animal or human for sensing the pressure of the body cavity. Tambour 16 must be constructed of a flexible material so that it will be responsive to pressure changes and a material which is impermeable to the non-radioactive fluid and in particular to water. A desirable material from the standpoint of flexibility and tissue compatibility is silicone rubber such as the elastomer sold under the trademark Silastic. However, extensive experimentation has shown that silicone rubber tambours cannot be used because of loss of fluid through the wall of the tambour. It was recently discovered that butyl rubber which has a low diffusion coefficient for water is a suitable material from which the tambour can be fabricated. This discovery is disclosed and claimed in the commonly assigned application cross-referenced above. The butyl rubber tambour can be coated with a thin coating of silicone rubber to provide better tissue compatibility. Tambour 16 is essentially a flexible container or sack which can be formed in any suitable shape such as cylindrical, disc-shaped, spheroidal or planar. As shown in FIG. 2, wire 60 can be placed in tambour 16 to give it suitable shape. Furthermore, a coiled spring (not shown) can be placed in neck portion 62 of tambour 16.

Sensor 10 is preferably constructed so that it is only responsive to pressure changes in the body cavity being sensed and is not responsive to ambient pressure changes. Tambour 14, which can be the same as tambour 16, provides this function and is filled with the same non-radioactive fluid as tambour 16. Accordingly, changes in ambient pressure will be exerted equally on both flexible tambours 14 and 16 making sensor 10 responsive only to changes in body cavity pressure sensed by tambour 16. Optionally, tambour 14 can be eliminated, the end of bellows tube 28 sealed, and chamber 20 filled with gas or evacuated to indicate absolute pressure. Also, for certain applications, tube 28 can be left open to communicate with the atmosphere.

Housing 12 as well as bellows support 26 and tubes 28, 40 and 44 are preferably constructed of titanium. Bellows 24 is preferably constructed of nickel and typically has a spring rate of 0.10 lbs/in. Radioactive material tube support 34, shielding plug 48 and shielding tube 50 preferably comprises tantalum shielding; however, tungsten, iridium, rhenium, platinum, rhodium, gold, or other suitable heavy metals can be used. All tubing, housing and diaphragm joints are suitably formed by epoxies, brazing, or the use of suitable gaskets, etc. Finally, the entire sensor can be coated with a thin coating of silicone rubber or placed in a silicone rubber boot if desired to assure tissue compatibility.

Changes in pressure of the body cavity being monitored compress tambour 16 and cause fluid to flow from tambour 16 through tubing 36 and into chamber 22 in housing 12. Tambour 16 offers effectively no resistance to the pressure change because of its flexible construction. Housing 12 provides a mechanical interface between the non-radioactive, pressure sensing fluid in tambour 16 and the ambient pressure compensating, non-radioactive fluid in tambour 14. Bellows 24 separates the two fluids and provides the force necessary to balance the body cavity pressure. As bellows 24 contracts under increasing body cavity pressure, it moves shielding tube 50 away from radioactive tube support 34. Since the count rate is directly dependent on the degree of shielding of radioactive material 42, the body cavity pressure can immediately be determined via the count rate.

Because of the unique construction of pressure sensor 10, no external leads are required and the sensor occupies very little space under the scalp so that it produces only a slight elevation thereof when the sensor is used for sensing intracranial pressure. Tambour 16 is placed through a burr hole within the skull and housing 12 is positioned outside the skull, but implanted under the scalp. A change in the volume of non-radioactive fluid in housing 12 is detected by measuring the change in radioactivity immediately adjacent to the skin caused by the movement of shielding tube 50. Thus, the skin does not have to be penetrated to obtain reliable pressure information. The quantity of the radioisotope utilized in the device is extremely small, typically less than one microcurie and results in surface dose rates to the scalp and skull which are on the order of 100 times less than the rates necessary to cause detectable changes in the most radiosensitive body tissue and thus will not adversely affect the adjacent skin or bone marrow.

The radioisotope used in the present invention should have a half life which is sufficiently long to give acceptable end-of-life pressure data. The radioisotope should also be safe as a source of radiation when used immediately beneath the scalp or within a body cavity. Another requirement is that the radioisotope must be detected efficiently which means that it must have a high skin transmissibility as well as a high detector efficiency.

The preferred radioisotope used in the present invention is promethium 145. Promethium has an 18 year half life and a soft gamma emission which can be easily transmitted through the skin and efficiently detected while being safely used in quantities necessary for statistical counting accuracy. Among other radioisotopes which can be used in the invention is holmium 163 which has a 40 to 60 year half life. The radioisotope is preferably mixed in an epoxy binder so that a solid radioactive material can be used.

Figure 3:
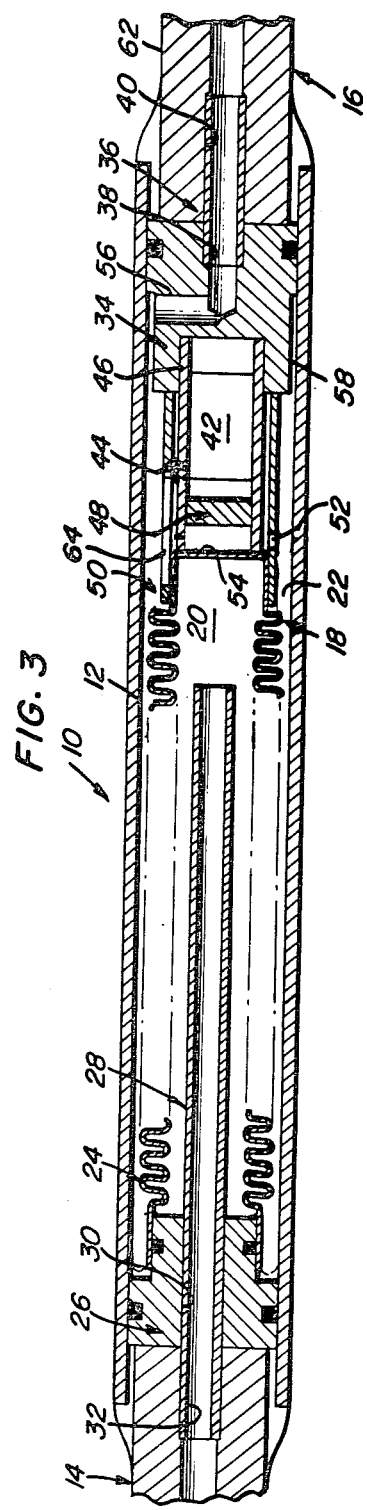
FIG. 3 is a vertical, cross-sectional view of a second embodiment of the pressure sensor apparatus of the present invention.

While the pressure sensor of the present invention has been illustrated primarily as an intracranial pressure sensor, it should be understood that the sensor is also useful in other body cavities in the treatment or care of animals and humans. Thus, valuable information may be derived from monitoring pressure in the vena cava, bladder, or some other body cavity. Further, use of the sensor is also applicable to determination of pressure difference or pressure in other applications, the foregoing details with respect to intracranial pressure being but a specific illustration of the application of the present invention to a particular problem and, in that sense, illustrative rather than limiting. Furthermore, while a preferred embodiment of the invention has been disclosed, it should be understood that the invention is not limited to such embodiment. For example, as shown in FIG. 3, source tube 44 can be connected to bellows 24 and shielding tube 50 to support 34. A window 64 can then be placed in shielding tube 50 and the count rate determined by placing a nuclear counter or crystal detector directly over the window as the radioactive material is moved by bellows 24 in response to pressure changes sensed by tambour 16. As a further example, tambour 16 can be replaced by a shunt tube containing a filter material which excludes particulate matter such as fibroblasts while permitting body fluid passage such as disclosed in commonly assigned application Ser. No. 489,000, filed on even date herewith, for APPARATUS FOR SENSING PRESSURE, by Glenn A. Meyer. Accordingly, the present invention should only be limited as defined in the appended claims.

What is claimed is:

1. A novel subcombination for use in a pressure sensor apparatus of the type that is embodied in the human body for obtaining, non-invasively, indications of internal body pressure, particularly intracranial pressure, including a two-component communication means operative upon relative movement therebetween capable of communicating internal body pressure indications non-invasively to the exterior of the body and, wherein said internal body pressure indications are detected in the body by a flexible fluid-filled tambour, said novel subcombination comprising an elongated, substantially cylindrical housing, a bellows support member connected to said housing at one end thereof and defining one of the end walls of said housing, a fluid filling the complete interior of said housing for communcating with the fluid-filled tambour through the other end of the housing to enable the transfer of fluid to the interior of the housing in proportion to the body pressure detected by the fluid-filled tambour, an elongated, substantially cylindrical elastic bellows suspended in said fluid within said housing, one end of said bellows being connected to said bellows support member for supporting said bellows coaxially within said housing and in suspension within said housing, with the substantially cylindrical side wall portion of said bellows extending from said one end of the bellows to the other end of the bellows, coaxial with said housing, said substantially cylindrical side wall portion of the bellows having a diameter less than the diameter of said housing defining an annular space therebetween, said other end of said bellows comprising a first attaching means for attaching a first component of a communication means and being spaced from the other end of the housing free of any fixed connection with said housing, said other end of the housing comprising a second attaching means for attaching a second component of a communication means free of any fixed connection with said bellows, said bellows and said housing defining a first chamber, including said annular space and said bellows and said bellows support means defining a second chamber isolated from the first chamber, each of said first and second chambers being filled completely with fluid, means for placing said first chamber in fluid communication with the fluid-filled tambour, means for permitting fluid within said second chamber to flow into and out of said second chamber upon actuation of said bellows in proportion to the amount of fluid flowing into said first chamber, the movement of said bellows taking place in a direction substantially parallel to the major axis of said housing.

2. The novel subcombination of claim 1, wherein said bellows is made of a metallic material.

3. The novel subcombination of claim 2, wherein said bellows is made of nickel.

4. The novel subcombination of claim 1, wherein said bellows has a spring rate of 0.10 lbs./in.

5. The novel subcombination of claim 1, wherein said side wall portion of said bellows is corrugated.

6. The novel subcombination of claim 1, wherein said means for placing said first chamber in fluid communication with the fluid-filled tambour comprises a first fluid conduit extending through the other end of said housing for permitting fluid to flow into and out of said first chamber, said means for permitting fluid within said second chamber to flow into and out of said second chamber, comprises a second fluid conduit extending through said bellows support means into said second chamber.

7. The novel subcombination of claim 1, further comprising two-component communication means contained within said housing for communicating the expansion and contraction movement of said bellows, the first of said two components connected with said first attaching means and suspended by said fluid in said first chamber, said first component movable with said bellows when said bellows expands and contracts, the second of said two components connected with said second attaching means within said first chamber, operatively associated with said first component, but free of physical attachment therewith, so that the relative movement of said first component with respect to said second component varies as a function of bellows movement in said housing, said communication means adapted to be sensed by a sensor means located external to said housing and free of physical interconnection therewith for sensing the relative position of said first and second components.

8. The novel subcombination of claim 1, wherein said housing is coated with silicone rubber for compatibility with human body tissue.

* * * * *